US007767686B2

(12) United States Patent
Podhajsky

(10) Patent No.: US 7,767,686 B2
(45) Date of Patent: Aug. 3, 2010

(54) METHOD OF USING ADENOSINE RECEPTOR BLOCKERS DURING TISSUE ABLATION

(75) Inventor: Ronald J. Podhajsky, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 399 days.

(21) Appl. No.: 11/367,909

(22) Filed: Mar. 3, 2006

(65) Prior Publication Data

US 2007/0207979 A1    Sep. 6, 2007

(51) Int. Cl.
*A61K 31/52* (2006.01)
*A01N 43/04* (2006.01)
(52) U.S. Cl. .................................. 514/263.34; 514/47
(58) Field of Classification Search .................. 514/263
See application file for complete search history.

(56) References Cited

U.S. PATENT DOCUMENTS

| 5,573,772 | A | 11/1996 | Downey et al. | |
| 5,840,990 | A | 11/1998 | Daluge et al. | |
| 6,586,413 | B2 | 7/2003 | Liang et al. | |
| 2002/0002142 | A1* | 1/2002 | Belardinelli et al. | 514/44 |
| 2005/0220799 | A1* | 10/2005 | Sitkovsky et al. | 424/184.1 |

OTHER PUBLICATIONS

Jones (Metastatic breast cancer: the treatment challenge, Clin Breast Cancer. Jun. 2008; 8(3): 224-33, printed p. 1, please see abstract).*
D. Haemmerich, "Hepatic radiofrequency ablation—an overview of an engineering perspective" *Minisymposium on applications of RF to Tissue Ablation*, San Francisco (Sep. 2004).
Adair, et al., "Adenosine infusion increases plasma levels of VEGF in humans", *BMC Physiology*, 5:10 (2005).
Anonymous, "Angiogenesis: A Common Pathway", *Cancer Research—Health Research Institute—Orlando Regional Healthcare* (Jun. 2005).
Linden J., "Adenosine in tissue protection and tissue regeneration", *Mol Pharmacol*, 67(5):1406-13 (May 2005) Abstract only.
Gadaleta C., et al. "Serum vascular endothelial growth factor concentrations in hepatocellular cancer patients undergoing percutaneously radiofrequency thermal ablation", *J. Chemother.* 16 Suppl. 5:8-10 (Nov. 2004). Abstract only.
Mujoomdar, M., et al., "Adenosine Stimulation of Proliferation of Breast Carcinoma Cell Lines: Evaluation of the [$^3$H]Thymidine Assay System and Modulatory Effects of the Cellular Microenvironment In Vitro" *Journal of Cellular Physiology* 201:429-438 (2004).
Linden, J., "Adenosine Receptors in Cancer", *Program 2 Member Descriptions* (date unknown).
Burić, N., et al., "Review and Analysis of Vasoconstrictors in Local Anesthetics Applied in Orofacial Surgery", *ACTA Stomatologica NAISSI* 19(43) (Sep. 2003).
Hines-Peralta, et al. "Improved Tumor Destruction with Arsenic Trioxide and Radiofrequency Ablation in Three Animal Models", *Radiology*, 240(1):82-89 (2006).
Washburn, et al., "Radiofrequency Tissue Ablation: Effect of Hepatic Blood Flow Occlusion on Thermal Injuries Produced in Cirrhotic Livers", Annals of Surgical Oncology, 10(7):773-777 (2003).
Feng, et al., "Adensine A2 Receptor Activation Attenuates Afferent Arteriolar Autoregulation During Adenosine Receptor Saturation in Rats", Hypertension 2007; 50; 744-749, (2007).
Keddie et al., "in vivo characterization of ZM 241385, a selective adenosine A2S receptor antagonist", European Journal of Pharmacology 301 (1996) 107-113.

* cited by examiner

*Primary Examiner*—Sreeni Padmanabhan
*Assistant Examiner*—Timothy E Betton

(57) ABSTRACT

A mammal undergoing an ablation procedure is treated for symptoms associated with adenosine by administering one or more adenosine receptor antagonists to the mammal prior to or during the procedure.

11 Claims, No Drawings

METHOD OF USING ADENOSINE RECEPTOR BLOCKERS DURING TISSUE ABLATION

BACKGROUND

1. Technical Field

The present disclosure relates to application of therapeutic agents for use during the treatment of mammalian, particularly human, ablation therapy or procedures, and more specifically to a treatment regimen that prevents or alleviates symptoms associated with adenosine.

2. Background of the Related Art

Energy based tissue ablation techniques are used clinically and in the operating room for therapeutic and surgical purposes. Such techniques eliminate tissue using energy sources such as laser, microwave, radiofrequency, high-intensity focused ultrasound, cryotherapy (such as freezing below −20 C), conductive heating, and the like. Although state-of-the-art energy based tissue ablation therapies and procedures have been successful in treating patients, these therapies and procedures are problematic in that they can lead to elevated concentrations of the purine nucleoside adenosine in treated areas. Adenosine can be problematic and counterproductive to the energy based therapy and/or overall treatment. For example, adenosine can promote metastasis disease, angiogenesis, tumor cell proliferation, vasodilatation, cardiac depression, low blood pressure, and other detrimental symptoms such as metastatic bloom. Moreover, adenosine can inhibit cell-mediated anti-tumor immune response.

SUMMARY

A method of treating symptoms associated with adenosine including administering to a mammalian subject undergoing an ablation procedure one or more agents in an amount effective in preventing or alleviating one or more symptoms associated with an elevated concentration of adenosine in the mammalian subject. In embodiments, the agent is one or more adenosine receptor antagonists such as 8SPT, MRS1754, MRS1220, MRE3008F20, MRS1523, ATL146e, or combinations of these adenosine receptor antagonists. In embodiments, the agent binds to one or more adenosine receptors in vivo.

In some embodiments, the agent is administered for the treatment of symptoms associated with adenosine such as inhibition of cell-mediated anti-tumor immune response, metastasis disease, angiogenesis, tumor cell proliferation, vasodilatation, cardiac depression, low blood pressure, and combinations of these symptoms or conditions.

In some embodiments, the agent can be administered for the treatment or prevention of low blood pressure, and/or prevention of metastasis disease.

In some embodiments, the ablation procedure is an energy based tissue ablation.

In some embodiments, the agent is one or more A1 adenosine receptor antagonists, including but not limited to: 1,3-dipropyl-8-cyclopentylxanthine, 8-(4-[({[(2-aminoethyl)amino]carbonyl)oxy]-phenyl}-1,3-dipropylxanthine, N(6)-Endonorbornan-2-yl-9-methyladenine, ((S)-(−)-8-(3-Oxocyclopentyl)-1,3-dipropyl-7H-purine-2,6-dione), (3-[(4-amino)phenethyl]-8-cyclopentylxanthine, 1,3-dipropyl-8-(dicyclopropylmethyl)xanthine, and combinations of these adenosine receptor antagonists.

In some embodiments, the agent is one or more A2 adenosine receptor antagonists, including but not limited to: 1,3-diallyl-8-(3,4,5-trimethoxystyryl)-7-methylxanthine, 8-(3,4, 5-trimethoxystyryl)-1,3,7-trimethylxanthine, 7-(2-phenylethyl)-5-amino-2-(2-furyl)-pyrazolo-[4,3-e]-1,2,4-triazolo[1,5-c]pyrimidine, 4-(2-[7-amino-2-(2-furyl[1,2,4]-triazolo[2,3-a[1,3,5]triazin-5-yl-)phenol), 8-(3-Chlorostyryl)caffeine, E)-1,3-dipropyl-7-methyl-8-(3,4-dimethoxystyryl)xanthine, enprofylline, 3-isobutyl-8-pyrrolidinoxanthine, [N-(4-cyanophenyl)-2-[4-(2,3,6,7-tetrahydro-2,6-dioxo-1,3-dipropyl-1H-purin-8-yl)-phenoxy]acetamide], and combinations of these adenosine receptor antagonists.

In some embodiments, the agent is one or more A3 adenosine receptor antagonists, including but not limited to: 3,6-dichloro-2'-(isopropoxy)4'-methylflavone, 6-phenyl-1,4-dihydropyridines, 6-carboxy-methyl-5,9-dihydro-9-methyl-2-phenyl-[1,2,4]-triazolo[5,1-a][2,7]naphthyridine, (3-(4-methoxyphenyl)-5-amino-7-oxo-thiazolo[3,2]pyrimidine), 9-chloro-2-(2-furanyl)[1,2,4]triazolo[1,5-c]quinazolin-5-amine, (2-(4-bromophenyl)-7,8-dihydro-4-propyl-1H-imidazo[2,1-i]purin-5(4H)-one dihydrochloride), and combinations of these adenosine receptor antagonists.

In some embodiments, the agent is administered in a pharmaceutical composition which includes a pharmaceutically acceptable carrier or diluent.

The present disclosure further relates to a method of treating symptoms associated with adenosine comprising administering to a mammalian subject undergoing an ablation procedure one or more adenosine receptor antagonists in an amount effective in preventing or alleviating one or more symptoms associated with adenosine. In some embodiments, the adenosine receptor antagonist includes 8SPT, MRS1754, MRS1220, MRE3008F20, MRS1523, ATL146e, or combinations of these adenosine receptor antagonists.

The present disclosure further relates to a method of treating symptoms associated with adenosine comprising administering to a mammalian subject undergoing an ablation procedure one or more adenosine receptor antagonists in an amount effective in preventing or alleviating one or more symptoms associated with adenosine, wherein the adenosine receptor antagonist includes 8SPT, MRS1754, MRS1220, MRE3008F20, MRS1523, ATL146e, or combinations of these adenosine receptor antagonists. In some embodiments, the ablation procedure is a radiofrequency ablation of a cancer tumor.

DETAILED DESCRIPTION

Adenosine is a purine nucleoside compound having the general formula:

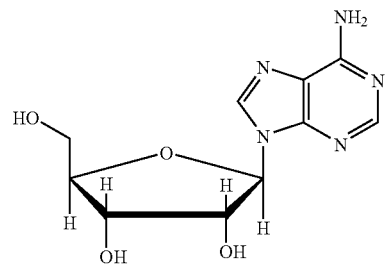

Adenosine or 9-B-D-ribofuranosyl-9H-purin-6-amine is prevalent throughout the body, and functions in various biochemical pathways by interacting with adenosine receptors that detect local changes in adenosine concentration.

The term "receptor" refers to a macromolecule capable of recognizing and selectively binding with a ligand, and which after binding the ligand, is capable of generating a physical or chemical signal that initiates the chain of events leading to the physiological response. Adenosine receptors are proteins found in animals and humans that can bind the ligand, adenosine, causing a physiological response. Adenosine receptors have been located in a variety of tissues and cells, including hippocampus, adipocytes, atrioventricle node, striatum, platelets, neutrophils, coronary vasculature and olfactory tubercule.

Four adenosine receptors are commonly referred to as A1, A2A, A2B, and A3. The stimulation of A1 receptors, among other things, can inhibit nerve cells, lower heart rate, slow AV nodal conduction, and promote vasoconstriction. The stimulation of A2A receptors is generally anti-inflammatory, and can be used to sense excessive tissue inflammation, and promote coronary vasodilatation. The stimulation of A2B generally promotes vasodilatation. The stimulation of A3 receptors, among other things, can both stimulate and inhibit cell growth, and promote tumor growth and angiogenesis.

Ligands that bind to the adenosine receptor causing the inhibition of the adenosine receptor physiological response are termed adenosine receptor antagonists. Likewise, ligands that bind to the adenosine receptor, thereby generating a physiological response that mimics the response caused by the adenosine receptor binding adenosine, are termed adenosine receptor agonists.

During energy based ablation procedures or therapies inflamed or damaged tissues can release adenine nucleotides that are converted to the purine nucleoside adenosine. The degradation of extracellular nucleotides results in an elevated concentration of adenosine in the treated area, which can be problematic and counterproductive to the therapy or treatment. Accordingly, as used herein an elevated concentration of adenosine in the mammalian subject refers to any increase in adenosine concentration in a mammalian body, including but not limited to any increase of adenosine concentration in one or more organs, tissues, systems, blood or blood parts, plasma, or the like. Moreover, an elevated concentration of adenosine in the mammalian subject refers to any higher than normal accumulation of adenosine that can detrimentally promote metastasis disease, angiogenesis, tumor cell proliferation, vasodilatation, cardiac depression, low blood pressure, and combinations of these detrimental symptoms, or which can inhibit cell-mediated anti-tumor immune response.

The present disclosure relates to methods for treating or alleviating symptoms associated with adenosine by administering to a mammalian subject undergoing an ablation procedure one or more agents in an amount effective in preventing or alleviating the symptoms associated with adenosine. As used herein the word "treat," "treating" or "treatment" refers to using the active agents or compositions of the present disclosure either prophylactically to prevent undesirable adenosine symptoms, or therapeutically to ameliorate an existing undesirable condition caused by adenosine. Treatment regimens in accordance with the present disclosure improve symptoms associated with adenosine through application of pre-selected antagonists to one or more adenosine receptors.

These methods are based upon the recognition that the inhibition of the adenosine receptor physiological response prior to, or during an ablation procedure provides beneficial effects that prevent or reduce angiogenesis, tumor cell proliferation, vasodilatation, cardiac depression, and/or low blood pressure. Furthermore, the inhibition of the adenosine receptor physiological response prior to or during an ablation procedure prevents or reduces likelihood of metastasis disease, or the limiting effect of adenosine on cell-mediated anti-tumor immune response. Blocking of adenosine receptors maximizes the desired protective benefits, while minimizing unwanted side effects from the stimulation of adenosine receptors, such as heart block, cardiac depression, or low blood pressure. Therefore, methods and compounds are described that can promote blocking of adenosine receptors.

In some embodiments, deactivation of the adenosine receptor occurs by contacting any adenosine receptor with one or more adenosine antagonists. Non-limiting examples of suitable adenosine antagonists include MRS 1754, MRS1220, MRE3008F20, MRS1523, ATL146e, either alone or in combination. Other receptor antagonist fall within the scope of the present disclosure including, but not limited to those adenosine antagonists listed in Table 1. Moreover, non-selective adenosine antagonists, such as 8-(p-sulfophenyl) theophylline (8SPT) can also be used in accordance with the present disclosure.

The adenosine receptor antagonists can be administered in amounts suitable to obtain the desired affect. For example, one or more adenosine receptor antagonists may be supplied in amounts sufficient to reduce or eliminate detrimental symptoms of adenosine, such as metastasis disease, angiogenesis, tumor cell proliferation, vasodilatation, cardiac depression, low blood pressure, and combinations of these detrimental symptoms. Moreover, adenosine receptor antagonists can be administered in amounts suitable to prevent inhibition of cell-mediated anti-tumor immune responses caused by adenosine. In some embodiments, adenosine receptor antagonists can be supplied in an amount from about 0.1 to 200 nmol/min/kg.

However, the specific dose level for any particular individual may depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those skilled in the art.

The adenosine receptor antagonists can be administered during any procedure or therapy that increases the amount of adenosine in a mammalian body. Illustrative non-limiting examples of such procedures or therapies include energy based tissue ablation such as cardiac ablation, transmyocardial revascularization, benign prostate hyperplasia therapy, ablation of endometriosis, breast cancer treatment, hemostasis, vessel sealing, endometrial ablation, skin resurfacing, metastasis ablation, image-guided treatments, noninvasive blood flow monitoring, surgical tissue welding, tissue reshaping, radiofrequency thermal ablation or radiofrequency ablation (RFA) (suitable for use in bone, and soft tissues such as liver, kidney, lung, heart, breast, lymph nodes, and nerve ganglia).

In accordance with the present disclosure, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection including perfusion and administration through catheters can be suitable. In some embodiments, methods of administration that allow rapid access to the tissue or organ being treated, such as intravenous injections for the treatment of myocardial infarction, is suitable. When an organ outside a body is being treated, perfusion can be a suitable method of administration.

Pharmaceutical compositions containing the active ingredient can be in any form suitable for the intended method of administration, including tablets, troches, lozenges, aqueous or oil suspensions, dispersible powders or granules, emulsions, hard or soft capsules, syrups or elixirs. Compositions intended for oral use can be prepared according to any method known to the art for the manufacture of pharmaceutical compositions. Tablets containing the active agent in admixture with non-toxic pharmaceutically acceptable excipients which are suitable for manufacture of tablets are acceptable.

Formulations for oral use can include hard gelatin capsules where the active ingredient is mixed with an inert solid diluent, or as soft gelatin capsules wherein the active ingredient is mixed with water or an oil medium.

The pharmaceutical compositions in accordance with the present disclosure can be in the form of a sterile injectable preparation, such as a sterile injectable suspension. This suspension may be formulated according to the known art using those suitable dispersing or wetting agents and suspending agents. In some embodiments, the sterile injectable preparation can also be a sterile injectable solution or suspension in a non-toxic parenterally acceptable diluent or solvent. Among the acceptable vehicles and solvents that may be employed are water, Ringer's solution and isotonic sodium chloride solution. In addition, suitable sterile fixed oils may be employed as a solvent or suspending medium.

The amount of active ingredient that may be combined with the carrier material to produce a single dosage form may vary depending upon the host treated and the particular mode of administration. For example, a time-release formulation intended for oral administration to humans may contain 20 to 200 μmoles of active material compounded with an appropriate and convenient amount of carrier material, which may vary from about 5 to about 95% of the total composition. In some embodiments, pharmaceutical composition can be prepared which provides easily measurable amounts for administration. For example, an aqueous solution intended for intravenous infusion should contain from about 20 to about 50 μ.moles of the active ingredient per milliliter of solution in order that infusion of a suitable volume at a rate of about 30 mL/hr can occur.

Formulations of the present disclosure suitable for oral administration may be presented as discrete units, such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form, such as a powder or granules, optionally mixed with a binder, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. Tablets may optionally be provided with an enteric coating, to provide release in parts of the gut other than the stomach.

Formulations for rectal administration may be presented as a suppository with a suitable base.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which can be made in accordance with techniques known in the art. The formulations can be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

In some embodiments, suitable unit dosage formulations are those containing a daily dose or unit, daily sub-dose, or an appropriate fraction thereof, of an adenosine receptor antagonist compound.

TABLE 1

Some A1, A2 and A3 receptor antagonists

| Abbreviation | Chemical Name |
|---|---|
| A1 ANTAGONISTS | |
| DPCPX | 1,3-dipropyl-8-cyclopentylxanthine |
| XAC | 8-(4-[({[(2-aminoethyl)amino]carbonyl)oxy]-phenyl}-1,3-dipropylxanthine |
| N-0861 | N(6)-Endonorbornan-2-yl-9-methyladenine |
| KFM 19 | ((S)-(-)-8-(3-Oxocyclopentyl)-1,3-dipropyl-7H-purine-2,6-dione) |
| BW-A844U | (3-[(4-amino)phenethyl]-8-cyclopentylexanthine |
| KF 15372 | 1,3-dipropyl-8-(dicyclopropylmethyl)xanthine |
| A2 ANTAGONISTS (Subtypes A2A and A2B) | |
| DATSX | 1,3-diallyl-8-(3,4,5-trim ethoxystyryl)-7-methylxanthine |
| DM TSX | 8-(3,4,5-trimethoxystyryl)-1,3,7-trimethylxanthine |
| SCH 58261 | 7-(2-phenylethyl)-5-amino-2-(2-furyl)-pyrazolo-[4,3-e]-1,2,4-triazolo[1,5-c] pyrimidine |
| ZM 241385 | 4-(2-[7-amino-2-(2-furyl[1,2,4]-triazolo[2,3-a[1,3,5]triazin-5-yl-)phenol) |
| CSC | 8-(3-Chlorostyryl)caffeine |
| KF17837 | E)-1,3-dipropyl-7-methyl-8-(3,4-dimethoxystyryl)xanthine |
| Enprofylline | 3,7-Dihydro-3-propyl-1H-purine-2,6-dione |
| IPDX | 3-isobutyl-8-pyrrolidinoxanthine |
| MRS 1754 | [N-(4-cyanophenyl)-2-[4-(2,3,6,7-tetrahydro-2,6-dioxo-1,3-dipropyl-1H-purin-8-yl)-phenoxy]acetamide] |
| A3 ANTAGONISTS | |
| MRS 1067 | 3,6-dichloro-2'-(isopropoxy)4'-methylflavone |
| MRS 1097 | 6-phenyl-1,4-dihydropyridines |
| L-249313 | 6-carboxy-methyl-5,9-dihydro-9-methyl-2-phenyl-[1,2,4]-triazolo [5,1-a][2,7]naphthyridine |
| L-268605 | (3-(4-methoxyphenyl)-5-amino-7-oxo-thiazolo [3,2]-pyrimidine) |
| CGS15943 | 9-chloro-2-(2-furanyl)[1,2,4]triazolo[1,5-c]quinazolin-5-amine |
| KF26777 | (2-(4-bromophenyl)-7,8-dihydro-4-propyl-1H-imidazo-[2,1-i]-purin-5(4H)-one dihydrochloride) |

The following examples are given for the purpose of illustrating the present disclosure and are not intended to limit the scope in any way.

EXAMPLE I

A 35 year old female weighing 130 pounds with stage 3 breast cancer is undergoing lumpectomy of 5 cm tumor located on right breast. After the lumpectomy, the margins of the tumor bed are cauterized with radiofrequency ablation (RFA), while patient is simultaneously administered adenosine receptor antagonist in an amount sufficient to, in vivo, block A1, A2, A3 adenosine receptors immediately adjacent to the tumor bed. The cauterization step is performed by delivering energy through a metal tube (probe) inserted into the tumor bed tissue. When the probe is in place, metal prongs open out to extend the reach of the therapy. Radio frequency energy causes atoms in the cells to vibrate and create friction and heat. Heating tumor bed tissue to 100° C. for 15 minutes with an RFA probe will likely generate approximately 1 cm margin of clear tissue surrounding the tumor bed. The drug administration step is performed by administering adenosine receptor antagonist to the affected tissue.

EXAMPLE II

A 63 year old female with atrial fibrillation (AF) is undergoing cardiac ablation to prevent abnormal electrical impulses from originating. While the surgeon is eliminating the tissue, that is causing the arrhythmia by energy ablation the female is administered a cocktail of A1, A2A, A2B and A3 adenosine receptor antagonists (1:1:1:1) in an amount sufficient to prevent symptoms associated with elevated adenosine.

EXAMPLE III

A 65 year old man suffering from an enlarged prostate undergoes transurethral needle ablation (TUNA), also called radiofrequency therapy that uses radio waves to heat and destroy a portion of the prostate that is blocking urine flow. A surgeon guides a catheter through the urethra and inserts needles into the prostate gland by manipulating the catheter. The surgeon applies radio waves to the prostate to heat and kill that portion of the prostate that is blocking urine flow. Simultaneously, a plurality of adenosine receptor antagonists are supplied to the patient. More specifically, the patient is administered KF 15372, DATSX, and MRS 1067 in amounts sufficient to prevent adenosine from binding to cells adjacent to the ablated prostate tissue.

While several embodiments of the disclosure are described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method for promoting blocking of an adenosine receptor in a mammalian subject undergoing an energy-based ablation procedure by administering adenosine receptor antagonists selected from 8SPT, MRS1754, MRS1220, MRE3008F20, MRS1523, ATL146e, or combinations thereof to the mammalian subject.

2. A method according to claim 1, wherein in vivo, the agent binds to one or more adenosine receptors.

3. A method according to claim 1, wherein the agent is administered in a pharmaceutical composition that includes a pharmaceutically acceptable carrier or diluent.

4. A method according to claim 1, wherein the mammalian subject is human.

5. A method according to claim 1, wherein the adenosine receptor antagonists is one or more A1 adenosine receptor antagonists.

6. A method according to claim 5, wherein the A1 adenosine receptor antagonists is selected from the group consisting of 1,3-dipropyl-8-cyclopentylxanthine, 8-(4-[({[(2-aminoethyl)amino]carbonyl)oxy]-phenyl}-1,3-dipropylxanthine, N(6)-Endonorbornan-2-yl-9-methyladenine, ((S)-(–)-8-(3-Oxocyclopentyl)-1,3-dipropyl-7H-purine-2,6-dione), (3-[(4-amino)phenethyl]-8-cyclopentylxanthine, 1,3-dipropyl-8-(dicyclopropylmethyl)xanthine, and combinations thereof.

7. A method according to claim 1, wherein the adenosine receptor antagonist is one or more A2 adenosine receptor antagonists.

8. A method according to claim 7, wherein the A2 adenosine receptor antagonists is selected from the group consisting of 1,3-diallyl-8-(3,4,5-trimethoxystyryl)-7-methylxanthine, 8-(3,4,5-trimethoxystyryl)-1,3,7-trimethylxanthine, 7-(2-phenylethyl)-5-amino-2-(2-furyl)-pyrazolo-[4,3-e]-1,2,4-triazolo[1,5- -c]pyrimidine, 4-(2-[7-amino-2-(2-furyl[1,2,4]-triazolo[2,3-a[1,3,5]triazin-5-yl-)phenol-), 8-(3-Chlorostyryl)caffeine, E)-1,3-dipropyl-7-methyl-8-(3,4-dimethoxystyryl)xanthine, enprofylline, 3-isobutyl-8-pyrrolidinoxanthine, [N-(4-cyanophenyl)-2-[4-(2,3,6,7-tetrahydro-2,6-dioxo-1,3-dipropyl-1H-pur-in-8-yl)-phenoxy]acetamide], and combinations thereof.

9. A method according to claim 1, wherein the adenosine receptor antagonist is one or more A3 adenosine receptor antagonists.

10. A method according to claim 9, wherein the agent is selected from the group consisting of 3,6-dichloro-2'-(isopropoxy)4'-methylflavone, 6-phenyl-1,4-dihydropyridines, 6-carboxy-methyl-5,9-dihydro-9-methyl-2-phenyl-[1,2,4]-triazolo[5,1-a][2,-7]naphthyridine, (3-(4-methoxyphenyl)-5-amino-7-oxo-thiazolo[3,2]pyrimidine), 9-chloro-2-(2-furanyl)[1,2,4]triazolo[1,5-c]quinazolin-5-amine, (2-(4-bromophenyl)-7,8-dihydro-4-propyl-1H-imidazo[2,1-i]purin-5(4H)-one dihydrochloride), and combinations thereof.

11. A method according to claim 1, wherein the ablation procedure is radiofrequency of a cancer tumor.

* * * * *